US012575749B2

(12) United States Patent
Deliwala

(10) Patent No.: US 12,575,749 B2
(45) Date of Patent: Mar. 17, 2026

(54) HETEROGENEOUS ARCHITECTURE INTEGRATION OF SILICON PHOTODIODE AND ACCELEROMETER

(71) Applicant: Analog Devices, Inc., Wilmington, MA (US)

(72) Inventor: Shrenik Deliwala, Andover, MA (US)

(73) Assignee: Analog Devices, Inc., Wilmington, MA (US)

( * ) Notice: Subject to any disclaimer, the term of this patent is extended or adjusted under 35 U.S.C. 154(b) by 450 days.

(21) Appl. No.: 16/933,396

(22) Filed: Jul. 20, 2020

(65) Prior Publication Data

US 2021/0045643 A1 Feb. 18, 2021

Related U.S. Application Data

(60) Provisional application No. 62/887,196, filed on Aug. 15, 2019.

(51) Int. Cl.
A61B 5/024 (2006.01)
A61B 5/00 (2006.01)

(52) U.S. Cl.
CPC ........ A61B 5/02427 (2013.01); A61B 5/6802 (2013.01); A61B 2562/0219 (2013.01); A61B 2562/0238 (2013.01); A61B 2562/028 (2013.01); A61B 2562/164 (2013.01); A61B 2562/227 (2013.01)

(58) Field of Classification Search
CPC .............. A61B 5/02427; A61B 5/6802; A61B 2562/0219; A61B 2562/0238; A61B 2562/028; A61B 2562/164; A61B 2562/227
See application file for complete search history.

(56) References Cited

U.S. PATENT DOCUMENTS

| | | | |
|---|---|---|---|
| 6,550,330 B1 * | 4/2003 | Waters | G01C 19/56 356/519 |
| 6,763,718 B1 * | 7/2004 | Waters | G01P 15/093 73/514.26 |
| 7,382,002 B2 | 6/2008 | Abbink | |

(Continued)

FOREIGN PATENT DOCUMENTS

CN         211789007 U   * 10/2020

OTHER PUBLICATIONS

Waters, R.L.; Jones, T.E. (2007) MEMS Navigation-Grade Electro-Optical Accelerometer. In Military Capabilities Enabled by Advances in Navigation Sensors (pp. 12-1 â 12-16). Meeting Proceedings RTO-MP-SET-104, Paper 12. Neuilly-sur-seine, France: RTO (Year: 2007).*

(Continued)

*Primary Examiner* — Jennifer Pitrak McDonald
*Assistant Examiner* — Moussa Haddad
(74) *Attorney, Agent, or Firm* — Schwegman Lundberg & Woessner, P.A.

(57) ABSTRACT

A novel, modified MEMS accelerometer with additional ability to measure optical radiation due to integration of silicon photodiode in the silicon cap. The silicon cap is used to protect the MEMS based accelerometer from the environment. The function of the cap is enhanced to include optical measurement. The entire sensor element including accelerometer and photodiode (XL+PD) occupies no more space than the XL alone.

14 Claims, 7 Drawing Sheets

(56) References Cited

U.S. PATENT DOCUMENTS

| | | | | |
|---|---|---|---|---|
| 8,740,802 | B2 | 6/2014 | Banet et al. | |
| 10,139,564 | B1 * | 11/2018 | Homeijer | H01S 5/0237 |
| 11,192,775 | B2 * | 12/2021 | Chang | B81B 3/0005 |
| 2008/0205762 | A1 | 8/2008 | Lapstun et al. | |
| 2010/0181467 | A1 * | 7/2010 | Chang | G01C 21/166 |
| | | | | 250/221 |
| 2013/0030259 | A1 * | 1/2013 | Thomsen | A61B 5/4824 |
| | | | | 600/301 |
| 2013/0186171 | A1 * | 7/2013 | Merrill, Jr. | G01P 21/00 |
| | | | | 73/514.16 |
| 2016/0141440 | A1 * | 5/2016 | Chun | H01L 31/18 |
| | | | | 257/82 |
| 2019/0280131 | A1 * | 9/2019 | Hettler | H04B 10/67 |

OTHER PUBLICATIONS

Tejada et al. "Microelectromechanical systems in 3D SOI-CMOS: sensing electronics embedded in mechanical structures", 2006 IEEE International Symposium on Circuits and Systems, May 21-24, 2006 (Year: 2006).*

* cited by examiner

HETEROGENEOUS ARCHITECTURE INTEGRATION OF SILICON PHOTODIODE AND ACCELEROMETER

CROSS-REFERENCE TO RELATED APPLICATIONS

This application is related to and claims the benefit of priority under 35 U.S.C. § 119(e) to U.S. Provisional Patent Application No. 62/887,196 entitled, "HETEROGENEOUS ARCHITECTURE INTEGRATION OF SILICON PHOTO-DIODE AND ACCELEROMETER" filed on Aug. 15, 2019 and related to U.S. patent application Ser. No. 14/500,129 entitled, "LOW FREQUENCY NOISE IMPROVEMENT IN PLETHYSMOGRAPHY MEASUREMENT SYS-TEMS" filed on Sep. 29, 2014, and U.S. Provisional Application No. 62/849,246, entitled "PLETHYSMOGRAPHY MEASUREMENT SYSTEMS AND APPARATUS" filed on May, 17, 2019, all of which are hereby incorporated by reference in their entirety.

FIELD OF THE DISCLOSURE

The present disclosure relates to medical equipment. More specifically, this disclosure describes apparatuses and systems for measuring plethysmography and other devices that detect biological events and, in particular, those for measure acceleration.

BACKGROUND

A plethysmograph (PPG) detector is a device for measuring biological events within body tissue. Using a plethysmograph (PPG) detector, and other devices for detecting biological events, operate by measuring changes in transmission or diffuse reflectance from the body tissue or subject under active illumination.

The radiation used for measuring plethysmograph (PPG) signals can span wavelengths from blue to infrared. In classic applications, light emitting diodes (LEDs) of two colors—often 660 nm and 940 nm—are used for measuring blood oxygen saturation. These devices are in large volume production and are readily available. In yet another application, a simple single-color LED—say at 940 nm—may be used to measure heart rate by measuring the periodic variation in a return signal. In some cases, a green LED is used to pick up variation in absorption caused by blood flow on the wrist.

FIGS. 1A-1B show functional block diagrams of exemplary plethysmograph (PPG) devices, in accordance with some embodiments of the disclosure provided herein. FIGS. 1A-1B show some of the common methods of measuring plethysmograph (PPG) signals. plethysmograph (PPG) signals are generated by measuring the changes in the transmission or diffuse reflectance of body tissue under active illumination by LED of a particular wavelength.

The beating of the heart changes both the mechanical dimensions of the arteries and also blood volume in those arteries. These effects lead to variation in the received light intensity. FIG. 2 is a functional graph of exemplary plethysmograph (PPG) devices in practice, in accordance with some embodiments of the disclosure provided herein. FIG. 2 shows a typical plethysmograph (PPG) signal and estimates of the signal required to measure parameters such as blood oxygen.

There is developing interest to measure plethysmograph (PPG) signals continuously by incorporating plethysmograph (PPG) sensors/systems in devices that can be attached to a subject, for example, wrist band, watch, in-the-ear buds, etc. In such applications, these devices have to function with very low power and every photon emitted from the LED is precious as it is a drain on a battery. Furthermore, space constraints force the use of small photodiodes to collect diffuse light coming from the tissue.

Since a heart beats at a relatively low frequency in the range of 0.5-5 Hz (30 to 300 beats per minute), this low frequency noise essentially limits the ability to measure the plethysmograph (PPG) signal. This becomes even more crucial for blood oxygen saturation (SpO2) systems where accurate determinations of both AC and DC components of the plethysmograph (PPG) signal must be made.

Within wearable devices, there is a demand for acceleration measurements. Acceleration measurement can improve the interpretation of the PPG measurement, as motions can corrupt the delicate PPG signals.

There is a demonstrated need in the art for a small footprint device which integrates optical measurements and corrects them using an integrated accelerometer. The inventors have recognized a need to conserve power and increase efficiency by also using a single ASIC.

Accordingly, the inventors perceive a need in the art for PPG system that optically taking PPG measurements with corroborating acceleration measurements to improve the results of plethysmograph (PPG) signals captured by such systems.

This overview is intended to provide an overview of subject matter of the present patent application. It is not intended to provide an exclusive or exhaustive explanation of the disclosure. Further limitations and disadvantages of conventional and traditional approaches will become apparent to one of skill in the art, through comparison of such systems with some aspects of the present disclosure as set forth in the remainder of the present application with reference to the drawings.

SUMMARY OF THE DISCLOSURE

A novel, modified MEMS accelerometer with additional ability to measure optical radiation due to integration of silicon photodiode in the silicon cap. The silicon cap is used to protect the microelectromechanical systems (MEMS) based accelerometer from the environment. The function of the cap is enhanced to include optical measurement. The entire sensor element including accelerometer and photodiode (XL+PD) occupies no more space than the accelerometer alone.

According to one aspect, the present disclosure is an apparatus for measuring PPG using one or more accelerometers with at least one photodiode built into the cap.

According to another aspect of the present disclosure, the bottom of the photodiode or the cap provides stable potential for the operation of accelerometer.

According to another aspect of the present disclosure, the bottom of the cap may be metalized to prevent any light from entering the accelerometer cavity.

According to another aspect of the present disclosure, a separate connection to the photodiode is provided directly on the cap and may also use the electrical connection provided thru the cap.

According to another aspect of the present disclosure, the accelerometer+photodiode is mounted on top of an ASIC.

According to another aspect of the present disclosure, the ASIC provides read-out of both accelerometer and photodiode.

According to alternate aspects of the present disclosure, the ASIC optionally provides synchronous blinking of LED for PPG based and other synchronous optical measurements.

According to alternate aspects of the present disclosure, the ASIC optionally provides ability to read the available ambient light.

According to another aspect of the present disclosure, the XL+PD are mounted on an ASIC and the entire assembly is co-packaged.

According to another aspect of the present disclosure, the package uses a clear mold compound to protect all the surfaces and the bond wires According to another aspect of the present disclosure, the package uses a clear glass to protect all the surfaces and the bond wires.

According to another aspect of the present disclosure, the package includes LED and other light sources.

According to another aspect of the present disclosure, the XL+PD is used in a wearable device.

According to another aspect of the present disclosure, the XL+PD is used in industrial measurement system to measure machine vibrations as well as the motion of the moving parts optically.

According to another aspect of the present disclosure, the accelerometer is a MEMS manufactured.

According to another aspect of the present disclosure comprises photodiodes and light source, in which a barrier is provided between the photodiode and light source to substantially reduce direct light from the light source.

According to another aspect of the present disclosure comprises photodiodes and light source, in which a barrier is provided between the photodiode and light source to specularly reflected light from the scattering medium to the photodiode(s).

According to another aspect of the present disclosure, the photodiodes substantially comprise a hole made in a semiconductor photodiode substrate.

According to another aspect of the present disclosure, the light source is placed such that light is emitted through the hole.

According to another aspect of the present disclosure, the photodiodes are confined to receive the light and collect therefrom concentrically arranged photodiodes.

According to another aspect of the present disclosure, the photodiodes substantially comprise a hole made in a semiconductor photodiode substrate.

According to another aspect of the present disclosure, the region between the photodiodes may be metallized to improve collection efficiency as some of the photons reaching the region between the photodiodes are reflected again thru the scattering medium to reach the photodiodes.

According to another aspect of the present disclosure, the PPG device comprises multiple wavelengths to measure PPG.

According to another aspect of the present disclosure, the present disclosure is used to estimate blood oxygen and blood pressure.

The drawings show exemplary XL+PD circuits and configurations. Variations of these circuits, for example, changing the positions of, adding, or removing certain elements from the circuits are not beyond the scope of the present disclosure. The illustrate configurations, and complementary devices are intended to be complementary to the support found in the detailed description.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

For a fuller understanding of the nature and advantages of the present invention, reference is made to the following detailed description of preferred embodiments and in connection with the accompanying drawings, in which.

DETAILED DESCRIPTION

Figure 1B:
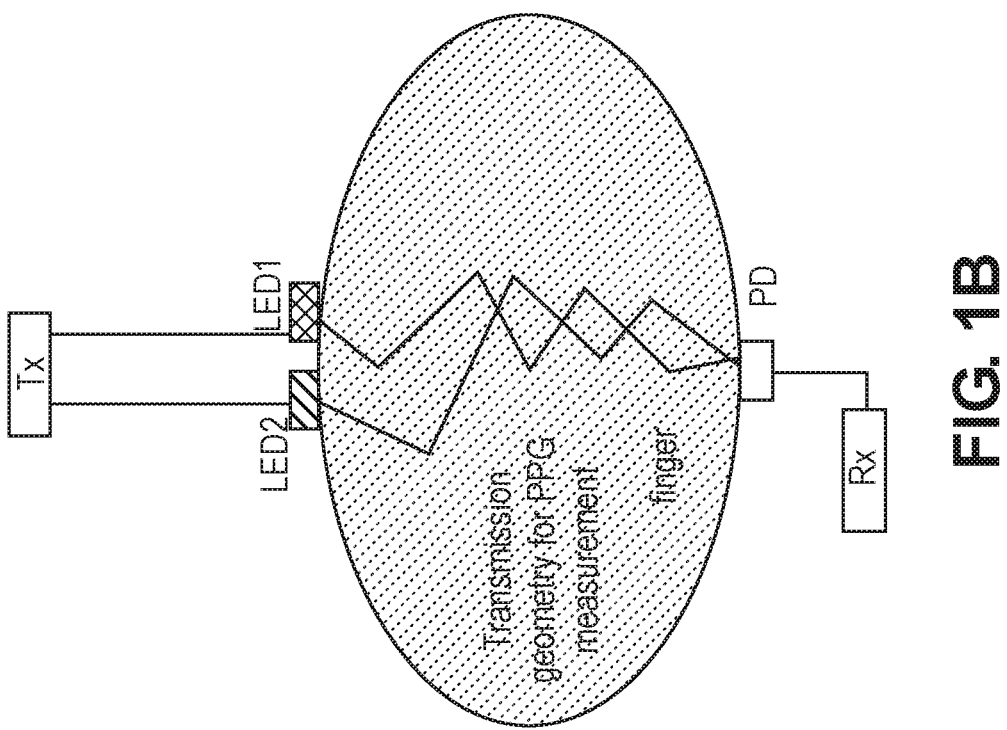
FIG. 1B shows functional block diagrams of exemplary plethysmograph (PPG) devices, in accordance with some embodiments of the disclosure provided herein.
Figure 1A:
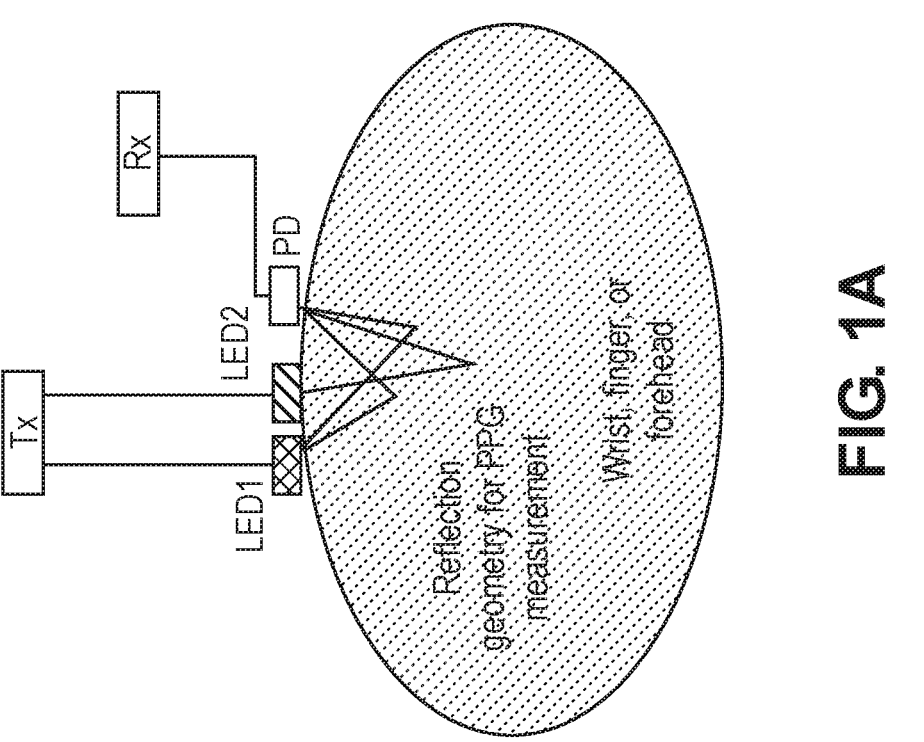
FIG. 1A shows functional block diagrams of exemplary plethysmograph (PPG) devices, in accordance with some embodiments of the disclosure provided herein.
Figure 2:
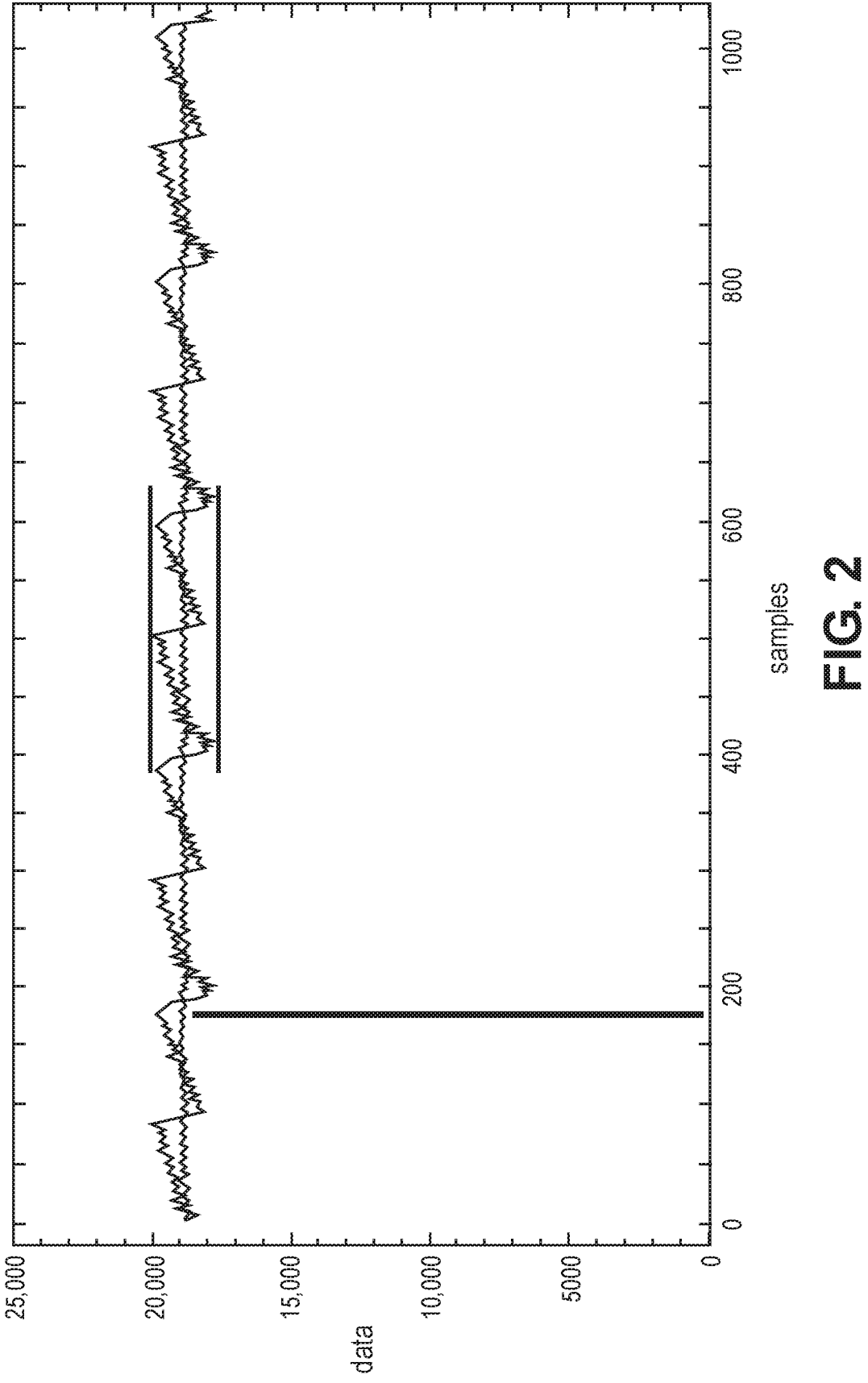
FIG. 2 is a functional graph of exemplary plethysmograph (PPG) devices in practice, in accordance with some embodiments of the disclosure provided herein.

The present disclosure relates to medical equipment. More specifically, this disclosure describes apparatuses and systems for measuring plethysmography and other devices that detect biological events and, in particular, those for measure acceleration. The inventor of the present disclosure contemplates enclosing a photodetector into the cap covering an accelerometer. The synergistic result achieves better accuracy, utility and power consumption.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

Embodiments of the present disclosure provide at least one source of PPG radiation and at least one sensor for detection of PPG radiation. The source of PPG radiation emits a portion of the PPG radiation toward a subject and another portion along an optical path for direct communication between the source of PPG radiation and the sensor. The sensor may develop a profile against which measurements from other PPG sensors, which receive light returning from the subject, may be compared. From this comparison, new PPG signals may be generated that exhibit lower noise than the PPG signals output by PPG sensors. These noise mitigation techniques may be used advantageously by a PPG system to generate more accurate measurements from compensation for movement measured by a proximate accelerometer, both of which are disposed on an ASIC and substrate.

This disclosure shows arrangement of photodiodes and light sources to reduce noise from dynamical light scattering in tissue due to the internal motion of the light scattering centers. This will improve both the quality and morphology of the PPG signal and make it less prone to this continuous and dynamic changes in the living tissue. This robustness to motion, which leads to higher quality PPG, and which in turn will lead to better measurement of physiological parameters such as blood oxygen and blood pressure as deduced from PPG signals. Furthermore, this also enables measurement of PPG (and by extension cardio-vascular parameters such as oxygen, pressure) in motion prone areas such as chest (breathing) and wrist which are both extremely convenient spots for monitoring physiology.

Photoplethysmography or PPG is a very popular method of measuring pulsatile changes in the blood volume due to pumping of blood from the heart. This is used to measure heart rate, changes in the heart rate as well as parameters such as SpO2 by measuring these signals at two or more wavelengths. Thus, multi-wavelength PPG techniques are well known and are in broad use. Many watches and wearable devices now have green LED (as well as other colors) to measure heart activity. Recently, it has also become apparent that accurately measuring the shape of the PPG signal can lead to even deeper insight into the hydrodynamics of the blood flow and empirically be correlated to blood pressure and other circulatory system parameters.

This has led to considerable effort to improve the quality of the PPG signal. There are two main aspects to it. To improve—i.e. to increase the SNR of—the pulsatile or the "AC" component of the PPG signal so that one can estimate parameters such as blood oxygen from non-conventional locations such as wrist or chest. Both locations on the body are useful commercially.

The other thrust to improve the SNR of the AC PPG signal is commercially driven by need to provide continuous and easy monitoring the conditions of the circulatory system such as blood pressure, arterial elasticity etc. This can be done from the analysis of the PPG pulse shape—so called morphological analysis—and other pulse related parameters.

This disclosure relates to arrangement of photodiodes and light sources that significantly improve SNR of the PPG by explicitly providing opto-electronic arrangements that significantly reduces the tissue induced noise. This disclosure is crucial to very important both above-mentioned thrusts.

A modified MEMS accelerometer with additional ability to measure optical radiation due to integration of silicon photodiode in the silicon cap is disclosed. The silicon cap is used to protect the MEMS based accelerometer from the environment. The function of the cap is enhanced to include optical measurement. The entire sensor element including accelerometer and photodiode (XL+PD) occupies no more space than the XL alone.

Furthermore, accelerometer element is often mounted on top of specialized read-out ASIC and packaged. A similar strategy is also adapted for the optical system with photodiode mounted on top of read-out ASIC for measuring photocurrents.

Figure 3:
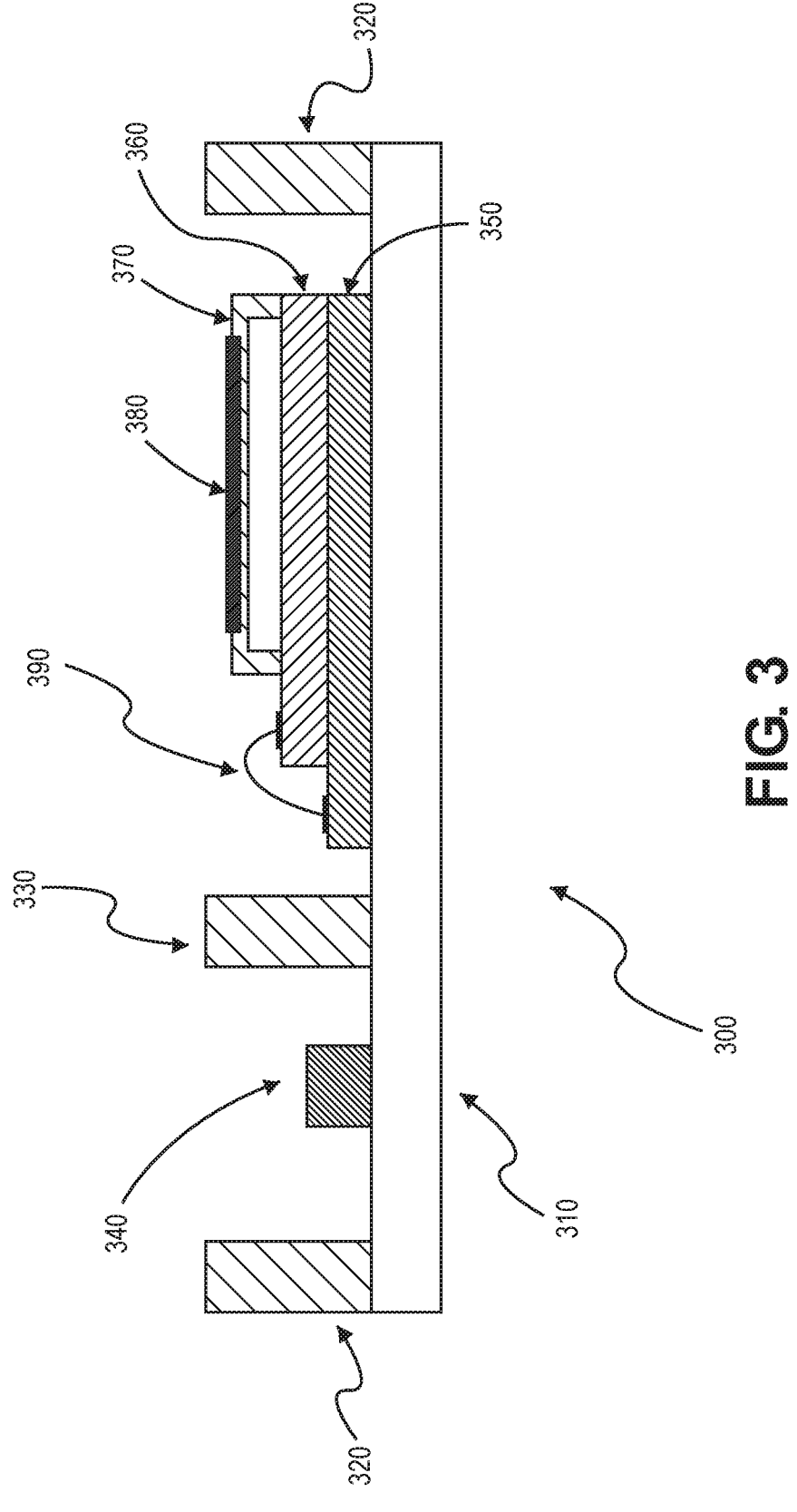
FIG. 3 is an exemplary sideview of an XL+PD apparatus, in accordance with some embodiments of the disclosure provided herein.

With the new XL+PD element, the new ASIC will have functionality to read both the photodiode and the accelerometer and this new sensor element is may be mounted on top of ASIC which now provides function for measuring both XL and PD. FIG. 3 is an exemplary sideview of an XL+PD apparatus, in accordance with some embodiments of the disclosure provided herein.

Accelerometer and photodiode system in package (XL+PD SIP) 300 comprise substrate 310, ambient blocking members 320, septum 330, light source 340, ASIC 350, accelerometer 360, cap 370, photodiode 380, and bond wire 390. In one or more embodiments, XL+PD SIP 300 is semiconductor package where a case surrounds a semiconductor chip on which device or integrated circuit is formed. In the present embodiment, XL+PD SIP 300 is System In Package (SIP) in which several chips form an electronic system.

In one or more embodiments, substrate 310 is a printed circuit board (PCB). A printed circuit board (PCB) mechanically supports and electrically connects electrical or electronic components using conductive tracks, pads and other features etched from one or more sheet layers of copper laminated onto and/or between sheet layers of a non-conductive substrate. Components are generally soldered onto the PCB to both electrically connect and mechanically fasten them to it. In other embodiments, substrate 310 is a made from wafer of silicon or polysilicon.

Ambient blocking members 320 comprise one or more polymers and are configured to block out any ambient light present in operation. In operation ambient blocking members are pressed against a subject's (or patient's) skin. Although designed to measure light emitted from light source 340 and interacting with a subject's tissue, mitigating ambient light typically results in better accuracy. In other embodiments, ambient blocking members 320 can be made from masking and etching a wafer of silicon thereby removing material for the circuitry and leaving the outer perimeter.

Septum 330 is produced in a similar manner. Septum 330 comprises one or more polymers which is configured to block the direct illumination from light source 340 to photodiode 380 which can be appreciated by one of ordinary skill in the art. In other embodiments, septum 330 can be made from masking and etching a wafer of silicon thereby removing material for the circuitry and leaving the intermediary blocking member.

In one or more embodiments, light source 340 is one or more light emitting diodes (LEDs). A light-emitting diode (LED) is a semiconductor light source that emits light when current flows through it. Electrons in the semiconductor recombine with electron holes, releasing energy in the form of photons. The color of the light (corresponding to the energy of the photons) is determined by the energy required for electrons to cross the band gap of the semiconductor. White light is obtained by using multiple semiconductors or a layer of light-emitting phosphor on the semiconductor device.

The radiation used for measuring plethysmograph (PPG) signals can span wavelengths from blue to infrared. In classic applications, light emitting diodes (LEDs) of two colors—often 660 nm and 940 nm—are used for measuring blood oxygen saturation. These devices are in large volume production and are readily available. In yet another application, a simple single-color LED—say at 940 nm—may be used to measure heart rate by measuring the periodic variation in a return signal. In some cases, a green LED is used to pick up variation in absorption caused by blood flow on the wrist.

In other embodiments, light source 340 is a broadband lamp source and an optical filter to select a narrow band spectral region that overlaps with the absorption region of the gas of interest. In this context narrow may be 50-300 nm bandwidth. In yet other embodiments these may include Microelectromechanical systems (MEMs) or mid IR LED sources, with or without an optical filter.

In one or more embodiments, ASIC 350 is an application-specific integrated circuit. An ASIC is an integrated circuit (IC) chip customized for a particular use, rather than intended for general-purpose use. For example, a chip designed to run in a digital voice recorder or a high-efficiency bitcoin miner is an ASIC. Application-specific standard product (ASSP) chips are intermediate between ASICs and industry standard integrated circuits. ASIC chips are typically fabricated using metal-oxide-semiconductor (MOS) technology, as MOS integrated circuit chips.

In one or more embodiments, accelerometer 360 comprises a complete 3-axis acceleration measurement system that operates at extremely low power consumption levels. It measures both dynamic acceleration, resulting from motion or shock, and static acceleration, such as tilt. Acceleration is reported digitally and the device communicates via the serial peripheral interface (SPI) protocol. Built-in digital logic enables autonomous operation and implements functionality that enhances system level power savings.

In some embodiments, the moving component of the sensor in the accelerometer 360 is a polysilicon surface-micromachined structure that is built on top of a silicon wafer. Polysilicon springs suspend the structure over the surface of the wafer and provide a resistance against acceleration forces. Deflection of the structure is measured using differential capacitors that consist of independent fixed plates and plates attached to the moving mass. Acceleration deflects the structure and unbalances the differential capacitor, resulting in a sensor output whose amplitude is proportional to acceleration. Phase sensitive demodulation determines the magnitude and polarity of the acceleration In some embodiments, accelerometer 360 has two operating modes: measurement mode for continuous, wide bandwidth sensing; and wake-up mode for limited bandwidth activity detection. In addition, measurement can be suspended altogether by placing the device in standby.

Measurement mode is the normal operating mode of the accelerometer 360. In this mode, acceleration data is read continuously and the accelerometer consumes less than 3 μA (typical) across its entire range of output data rates of up to 400 Hz using a 2.0 V supply.

The ability to continuously output data from the minimum 12.5 Hz to the maximum 400 Hz data rate while still delivering less than 3 μA (typical) of current consumption is how the accelerometer 360 as an ultralow power accelerometer. Other accelerometers derive low current by using a specific low power mode that power cycles acceleration sensing. The result is a small effective bandwidth in the low power modes and undersampling of input data; therefore, unwanted aliasing can occur. Under-sampling and aliasing do not occur with the accelerometer 360 because it continuously samples the full bandwidth of its sensor at all data rates.

Wake-up mode is ideal for simple detection of the presence or absence of motion at extremely low power consumption (270 nA at a 2.0 V supply voltage). Wake-up mode is useful particularly for implementation of a motion activated on/off switch, allowing the rest of the system to be powered down until activity is detected.

Wake-up mode reduces current consumption to a very low level by measuring acceleration only about six times per second to determine whether motion is present. If motion is detected, the accelerometer can respond autonomously in the following ways:

Switch into full bandwidth measurement mode

Signal an interrupt to a microcontroller

Wake up downstream circuitry, depending on the configuration

In wake-up mode, all accelerometer features are available with the exception of the activity timer. All registers can be accessed, and real-time data can be read and/or stored in the FIFO.

Placing the accelerometer 360 in standby suspends measurement and reduces current consumption to 10 nA (typical). Pending interrupts and data are preserved and no new interrupts are generated.

In one or more embodiments, cap 370 comprises silicon which encases and covers the accelerometer 360 in order to protect it from the environment. The operation of which will be discussed in more detail later in the disclosure. In other embodiments, cap 370 may comprise polysilicon, silicon nitride, or silicon dioxide. Any other suitable material is not beyond the scope of the present invention. The choice of material characteristics depends on the configuration and disposition of the photodiode 380, which will be discussed in greater detail later in the disclosure.

Photodiode (PD) 380 is a sensor of light or other electromagnetic energy. In some embodiments, photodiode 380 has p-n junctions that converts light photons into current. The absorbed photons make electron—hole pairs in the depletion region, which is used detect received light intensity. In some embodiments, photodiode 380 is any generic photodetector, photo-sensor or phototransistors. However, any light detecting means, e.g., avalanche, photo-multiplier tube, etc. is not beyond the scope of the present disclosure.

In one or more embodiments, bond wire 390 comprises a highly conductive material and is configured to provide electrical communication from accelerometer 360 to ASIC 350 through bond pads which are well known in the art. The functionality of which will be discussed in greater detail later in the disclosure.

Figure 4:
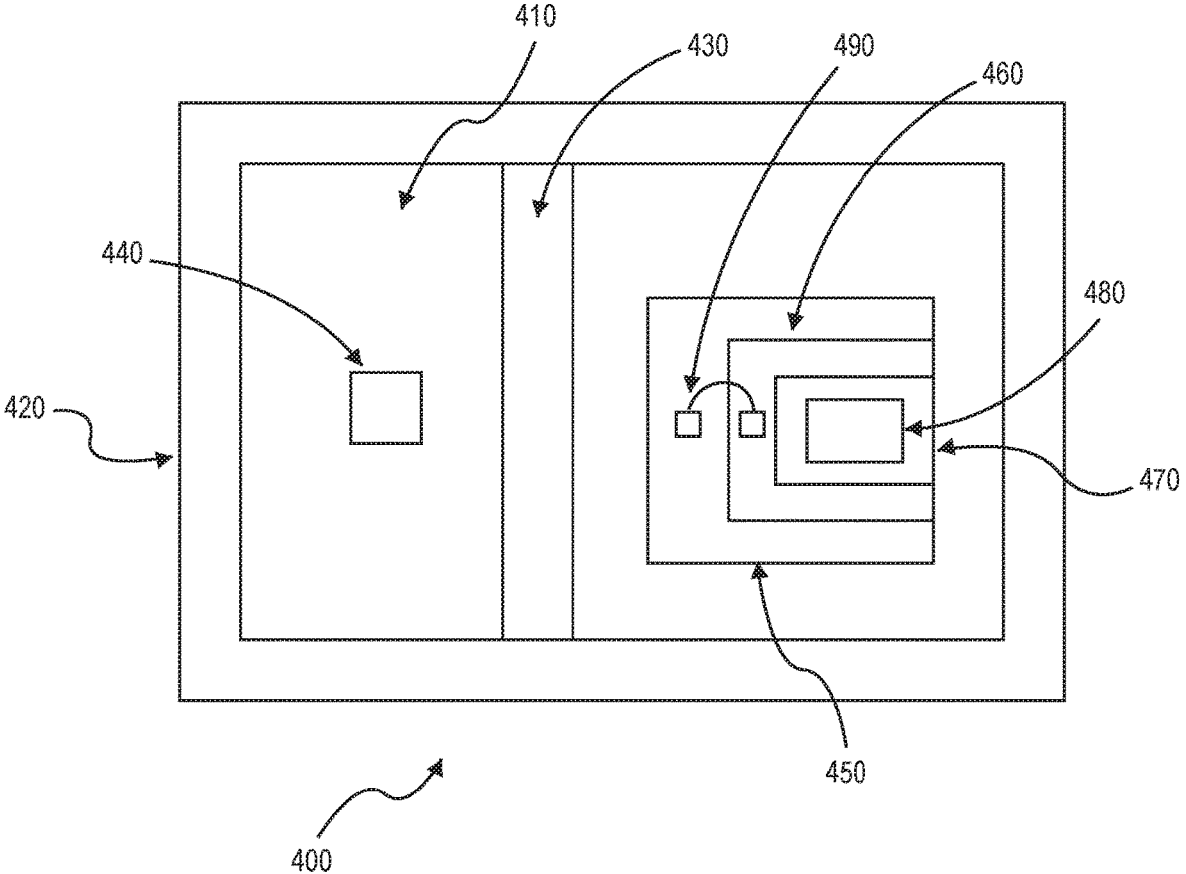
FIG. 4 is an exemplary top down view of an XL+PD apparatus, in accordance with some embodiments of the disclosure provided herein.

FIG. 4 is an exemplary top down view of an XL+PD apparatus, in accordance with some embodiments of the disclosure provided herein. Accelerometer and photodiode system in package (XL+PD SIP) 400 comprises substrate 410, ambient blocking members 420, septum 430, light source 440, ASIC 450, accelerometer 460, cap 470, photodiode 480, and bond wire 490.

In some embodiments, XL+PD SIP 400 is semiconductor package where a case surrounds a semiconductor chip on which device or integrated circuit is formed. In the present embodiment, XL+PD SIP 400 is System In Package (SIP) in which several chips form an electronic system.

In one or more embodiments, substrate 410 is a printed circuit board (PCB). A printed circuit board (PCB) mechanically supports and electrically connects electrical or electronic components using conductive tracks, pads and other features etched from one or more sheet layers of copper laminated onto and/or between sheet layers of a non-conductive substrate. Components are generally soldered onto the PCB to both electrically connect and mechanically fasten them to it. In other embodiments, substrate 410 is a made from wafer of silicon or polysilicon.

Ambient blocking members 420 comprise one or more polymers and are configured to block out any ambient light present in operation. In operation ambient blocking members are pressed against a subject's (or patient's) skin. Although designed to measure light emitted from light source 440 and interacting with a subject's tissue, mitigating ambient light typically results in better accuracy. In other embodiments, ambient blocking members 420 can be made from masking and etching a wafer of silicon thereby removing material for the circuitry and leaving the outer perimeter.

Septum 430 is produced in a similar manner. Septum 430 comprises one or more polymers which is configured to block the direct illumination from light source 440 to photodiode 480 which can be appreciated by one of ordinary skill in the art. In other embodiments, septum 430 can be made from masking and etching a wafer of silicon thereby removing material for the circuitry and leaving the intermediary blocking member.

In one or more embodiments, light source 440 is one or more light emitting diodes (LEDs). A light-emitting diode (LED) is a semiconductor light source that emits light when current flows through it. Electrons in the semiconductor recombine with electron holes, releasing energy in the form of photons. The color of the light (corresponding to the energy of the photons) is determined by the energy required for electrons to cross the band gap of the semiconductor. White light is obtained by using multiple semiconductors or a layer of light-emitting phosphor on the semiconductor device.

In one or more embodiments, ASIC 450 is an application-specific integrated circuit. An ASIC is an integrated circuit (IC) chip customized for a particular use, rather than intended for general-purpose use. For example, a chip designed to run in a digital voice recorder or a high-efficiency bitcoin miner is an ASIC. Application-specific standard product (ASSP) chips are intermediate between ASICs and industry standard integrated circuits. ASIC chips are typically fabricated using metal-oxide-semiconductor (MOS) technology, as MOS integrated circuit chips.

In one or more embodiments, accelerometer 460 comprises a complete 3-axis acceleration measurement system that operates at extremely low power consumption levels. It measures both dynamic acceleration, resulting from motion or shock, and static acceleration, such as tilt. Acceleration is reported digitally and the device communicates via the serial peripheral interface (SPI) protocol. Built-in digital logic enables autonomous operation and implements functionality that enhances system level power savings.

In one or more embodiments, cap 470 comprises silicon which encases and covers the accelerometer 460 in order to protect it from the environment. The operation of which will be discussed in more detail later in the disclosure. In other embodiments, cap 470 may comprise polysilicon, silicon nitride, or silicon dioxide. Any other suitable material is not beyond the scope of the present invention. The choice of material characteristics depends on the configuration and disposition of the photodiode 480, which will be discussed in greater detail later in the disclosure.

Photodiode (PD) 480 is a sensor of light or other electromagnetic energy. In some embodiments, photodiode 480 has p-n junctions that converts light photons into current. The absorbed photons make electron-hole pairs in the depletion region, which is used detect received light intensity. In some embodiments, photodiode 480 is any generic photodetector, photo-sensor or phototransistors. However, any light detecting means, e.g., avalanche, photo-multiplier tube, etc. is not beyond the scope of the present disclosure.

In one or more embodiments, bond wire 490 comprises a highly conductive material and is configured to provide electrical communication from accelerometer 460 to ASIC 440 through bond pads which are well known in the art. The functionality of which will be discussed in greater detail later in the disclosure.

PD 480 is built into the cap 470 as shown. There may be a bond-wire from the cap to the ASIC 440 to electrically connect the photodiode 480 or the connection to the photodiode 480 may be thru the cap 470 and provided with the accelerometer 460 connection. More than one photodiode may be built into the cap. This simply increases the number of electrical connections on the cap.

For a good functioning of accelerometer 460, cap 470 is generally biased to a fixed potential. This prevents stray electric fields and charges to change the motion of the highly sensitive MEMS beams. Read-out of the photodiode 480 currents also require biasing of the photodiode 480. One may bias the "bottom" of the cap 470—defined as one facing the accelerometer 460 cavity—to the correct potential for the operation of the accelerometer 460. The potential on the top of the cap 470—the facing the outside word so that light is received, may be either at the same potential or at any potential that provides reverse biasing of the photodiode 480 junction.

The advantages of the present configuration will now be enumerated. A single package for XL+PD provides substantial saving in area used by sensors. The stacking greatly reduces the real estate (or footprint) required by the system device. As such, the system can be incorporated into an increased number of portable or wearable devices.

Another advantage is that there is substantial saving in computational energy as the accelerometer and photodiode data never miss synchronization—a common occurrence with separate read-out ASICs for XL and PD. The state of the art requires to ASICs with two individual but disparate clocks. During readout during both, this can produce a beating phenomenon. A combined dedicated ASIC 450 requires less (half) the power of two ASICs usually required to process the analog output of a separate XL+PD.

Another advantage is that it is easy to provide synchronized measurement of accelerometer and PD for improved measurement of the sensor fusion data. Sensor data fusion comprise data that is interpreted as taken at substantially the same time. For example, a device may discount a measured PPG signal if the XL output is in constant motion thereby reducing its accuracy. Other examples are discussed throughout the disclosure.

Another advantage is that it is easy to provide built-in functionality to trigger read-out of one sensor when a particular set of conditions are met for the other sensor. For example, optical power from the LED may be automatically reduced when XL's output shows lack of motion.

Figure 5:
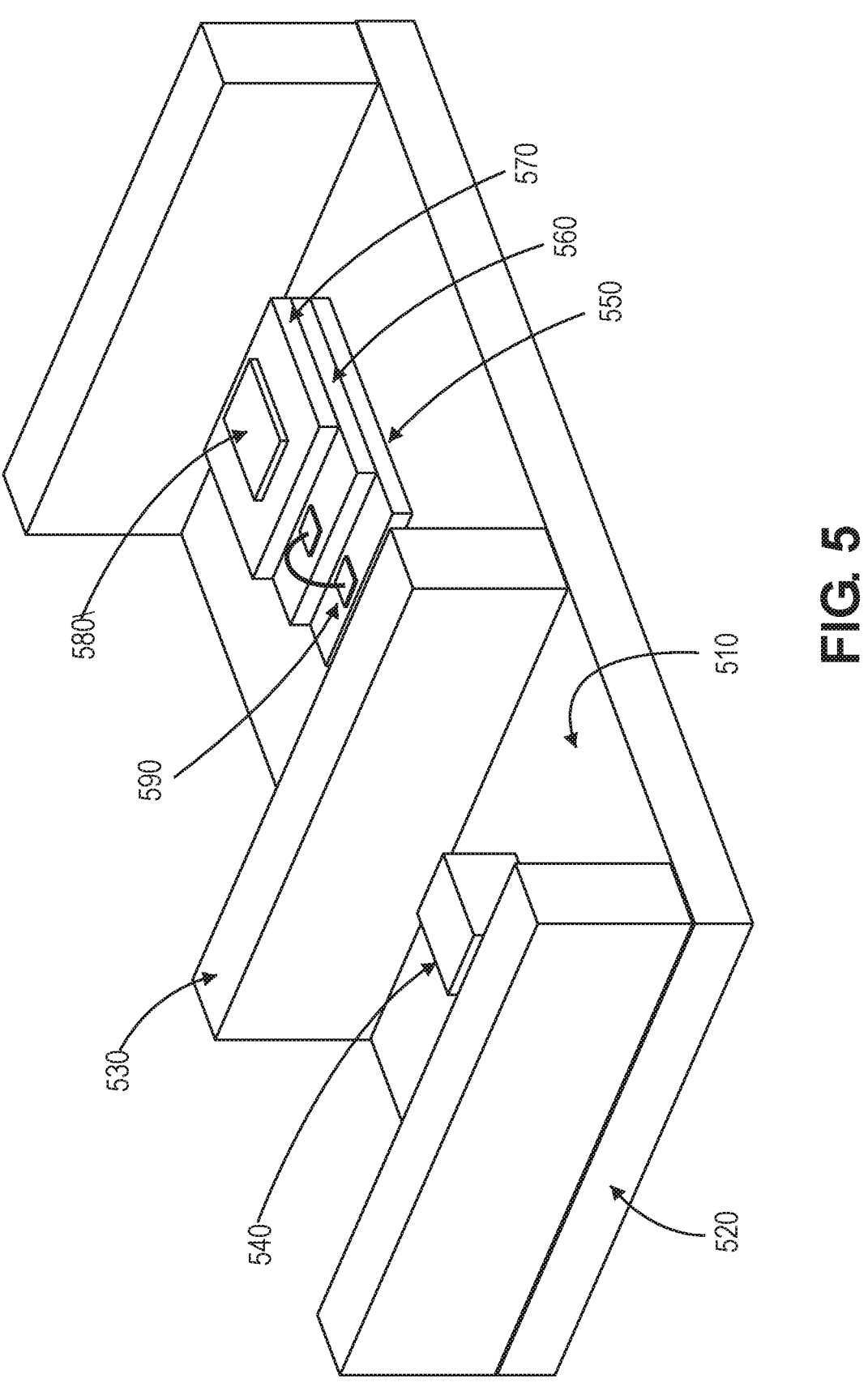
FIG. 5 depicts an exemplary isometric perspective of an XL+PD apparatus, in accordance with some embodiments of the disclosure provided herein.

FIG. 5 depicts an exemplary isometric perspective of an XL+PD apparatus, in accordance with some embodiments of the disclosure provided herein. Accelerometer and photodiode system in package (XL+PD SIP) 500 comprises substrate 510, ambient blocking members 520, septum 530, light source 540, ASIC 550, accelerometer 560, cap 570, photodiode 580, and bond wire 590.

As described, XL+PD SIP 500 can be semiconductor package where a case surrounds a semiconductor chip on which device or integrated circuit is formed. In the present embodiment, XL+PD SIP 500 is System In Package (SIP) in which several chips form an electronic system.

Substrate 510 can be a printed circuit board (PCB). In other embodiments, substrate 510 is a made from wafer of silicon or polysilicon.

Ambient blocking members 520 comprise one or more polymers and are configured to block out any ambient light present in operation. In other embodiments, ambient blocking members 520 can be made from masking and etching a wafer of silicon thereby removing material for the circuitry and leaving the outer perimeter.

As previously described septum 530 comprises one or more polymers which is configured to block the direct illumination from light source 540 to photodiode 580 which can be appreciated by one of ordinary skill in the art. In other embodiments, septum 530 can be made from masking and etching a wafer of silicon thereby removing material for the circuitry and leaving the intermediary blocking member.

Light source 540 is one or more light emitting diodes (LEDs) or a plurality of wavelength, as can be appreciated by one of ordinary skill in the art. In one or more embodiments, ASIC 550 is an application-specific integrated circuit. An ASIC is an integrated circuit (IC) chip customized for a particular use, rather than intended for general-purpose use.

In one or more embodiments, accelerometer 560 comprises a complete 3-axis acceleration measurement system that operates at extremely low power consumption levels. In one or more embodiments, cap 570 comprises silicon which encases and covers the accelerometer 560 in order to protect it from the environment. Photodiode (PD) 580 is a sensor of light or other electromagnetic energy.

In some embodiments, bond wire 590 comprises a highly conductive material and is configured to provide electrical communication from accelerometer 560 to ASIC 540 through bond pads which are well known in the art. The functionality of which will be discussed in greater detail later in the disclosure.

Figure 6:
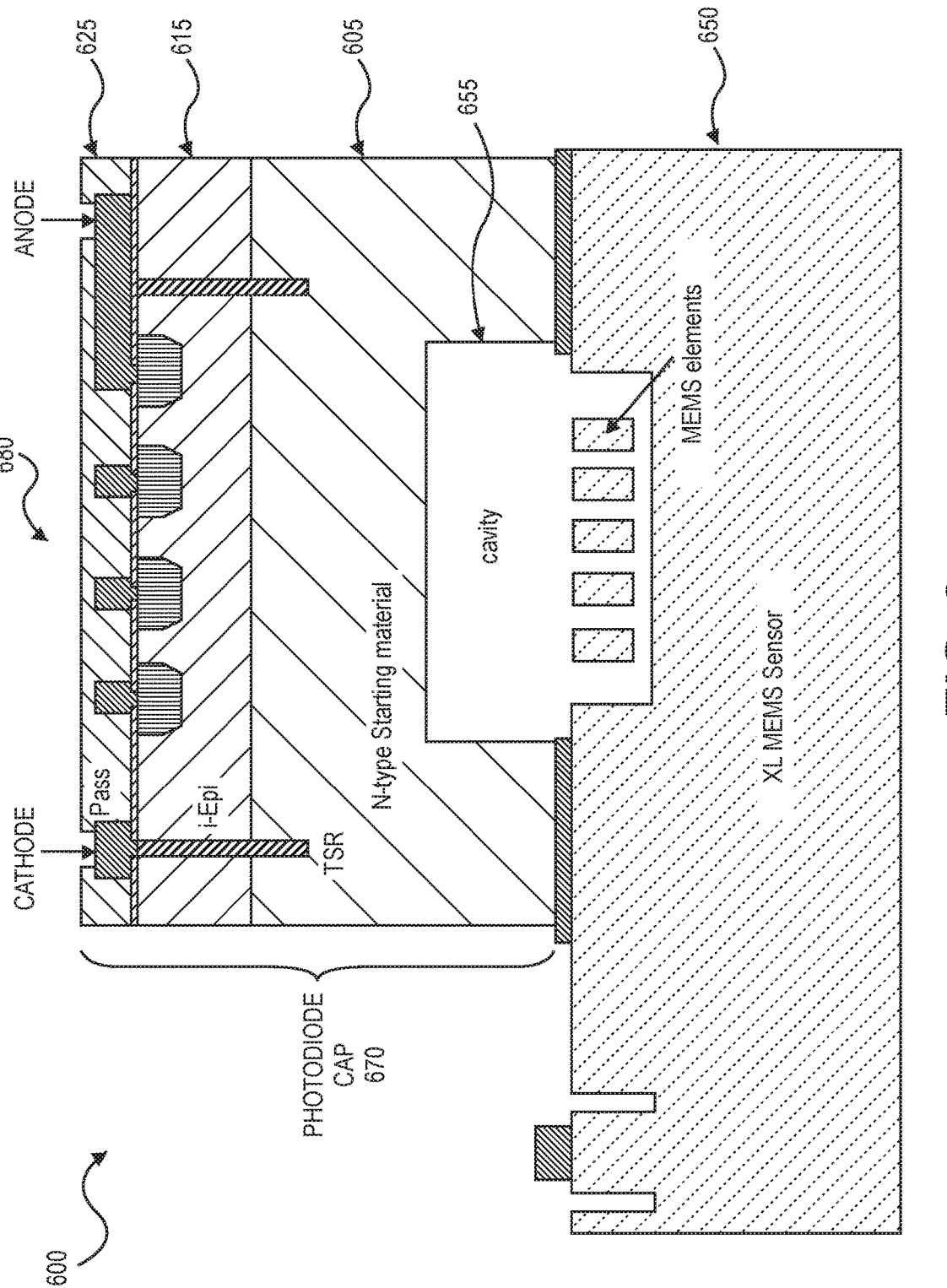
FIG. 6 illustrates an exemplary manufacturing stack of an XL+PD device 600, in accordance with some embodiments of the disclosure provided herein; and, FIG. 7 depicts an exemplary 3-dimensional perspective of an XL+PD apparatus, in accordance with some embodiments of the disclosure provided herein.

FIG. 6 illustrates an exemplary manufacturing stack of an XL+PD device 600, in accordance with some embodiments of the disclosure provided herein. XL+PD device 600 comprises XL MEMS sensor 650, cap 670, and photodiode 680.

Cap 670 comprises cavity 655, N-type layer 605, Epitaxial layer 615 and passivation layer 625. In one or more embodiments, cap 670 is manufactured using a flip-chip approach. N-type material 605 can be grown on an intrinsic Epitaxial layer. N-type material 605 is etched out to create cavity 655, necessary for proper XL MEMS 650 sensor operation.

The device is flipped and bonded to XL MEMS 650. Photodiode 680 is produced by etching into the i-Epi layer 615 and depositing P-type electrodes. Various methods known in the art, such as bumping, can be used to create the anode and cathode. A passivation and/or dielectric layer is then used to cover and protect the photodiode 680.

As was previously described, the cap 670 and/or photodiode 680 can be biased separately or together. This is achieved by a deep connection to the bulk of N-type material 605. During fabrication a through silicon resistor (TSR) is created by trenching out epi-layer 615 down in to the bulk of the N-type material 605. To preserve conductivity, the walls are lined with glass to preclude shorting or crosstalk in the epi-layer 615. Other manufacturing techniques, such as, VIAs, chemical etching, etc., are not beyond the scope of the present invention.

Figure 7:
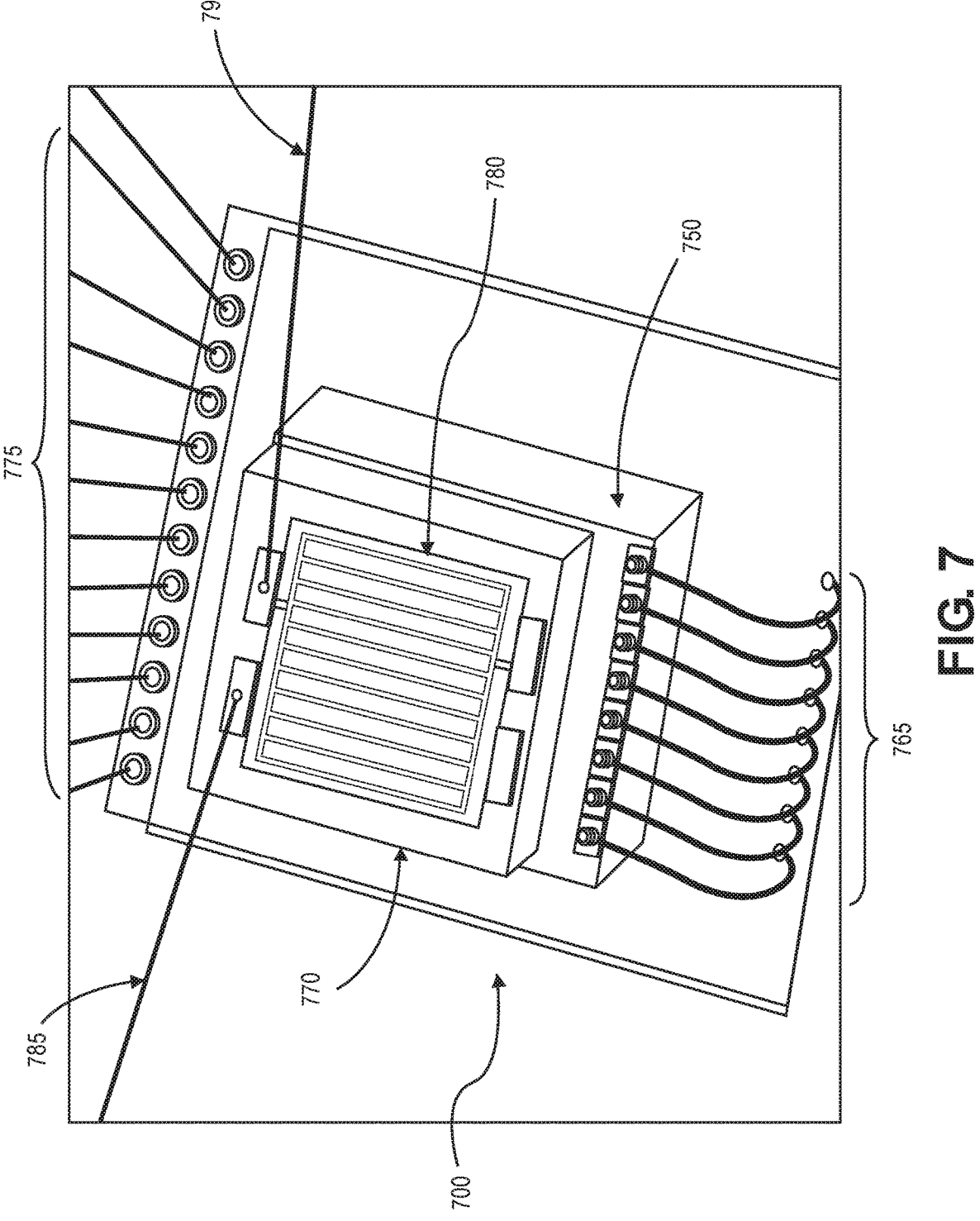

FIG. 7 depicts an exemplary 3-dimensional perspective of an XL+PD device 700, in accordance with some embodiments of the disclosure provided herein. XL+PD device 700 comprises ASIC accelerometer 750, cap 770, photodiode 780, anode wire 785 and cathode wire 795.

In practice, conductors 765 engender electrical communication between XL 750 and ASIC, in one or more embodiments. Other fabrications methods are not beyond the scope of the present disclosure, such as, VIAs, bump pads, traces, etc. Similarly, wires 775 are used to connect the ASIC to the package.

Hetero-integration affords the benefits of integration: signal proximity, size, mix of capabilities with the benefit of disintegration: using each optimized process in nearly its native state. Rather than dropping MEMS in photodiode circuit process, capping serves as an intermediary.

Heterogeneous processing can also combine the sensor functionality of the MEMS inertial and optical photodetector processes. These combined accelerometers and photodiodes have comparable characteristics to those obtained in single sensor type processes. Existing ASIC can be processing data of both multiple types of data.

In one or more embodiments, cavity process is optimized for defect reduction. In other embodiments, thickness requirements are analyzed and, if needed, reduction strategies are implemented. In yet other embodiments, ASIC requirements are paired with and meet XL application needs in next generation architecture. Additionally, devices can comprise additional bond pads, complimentary clock, and/or Z-clock amplitude.

While the following areas are the intended application, others are not beyond the scope of the present disclosure: health and wellness, such as, system level solutions for Optical Heart Rate, SpO2, ECG, EDA; clinical remote health monitoring, such as, power efficient/clinical grade product designed to support wireless/battery operated monitoring devices including, ECG, SpO2, Respiration and Supporting system level components including, M3/M4 Processors, PMU, and MBAN/BLE Radio; and, VSM Health Platform with a full multi-sensor platform including: ECG, PPG, EDA/GSR, activity, and temperature.

In addition to the preceding wearables, the inventor also envisions the present disclosure being placed in wearables and remote monitoring chest patches.

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure are set forth in the proceeding in view of the drawings where applicable.

SELECT EXAMPLES

Example 1 provides a single package accelerometer and photodiode comprising an accelerometer having a top portion and a bottom portion, a cap having a top portion and bottom portion configured to cover at least part of the top portion of the accelerometer and, a photodiode having a top portion and bottom portion disposed in and comprised by the cap.

Example 2 provides a single package accelerometer and photodiode of example 1 wherein the cap further comprises a first electrical connection configured for biasing protection of the accelerometer.

Example 3 provides a single package accelerometer and photodiode of example 1 wherein the bottom portion of the photodiode further comprises an electrical connection configured for biasing protection of the accelerometer.

Example 4 provides a single package accelerometer and photodiode of example 3 further comprising a second electrical connection in electrical communication with the photodiode.

Example 5 provides a single package accelerometer and photodiode of example 4, wherein the second electrical connection is configured to pass through the cap.

Example 6 provides a single package accelerometer and photodiode of example 1 wherein the bottom portion of the cap further comprises a metalized layer configure to prevent light from passing into the accelerometer.

Example 7 provides a single package accelerometer and photodiode of example 1 further comprising bond pad disposed in the accelerometer.

Example 8 provides a single package accelerometer and photodiode of example 7 further comprising an ASIC having bond pads.

Example 9 provides a single package accelerometer and photodiode of example 8, wherein the ASIC is in electrical communication with the accelerometer and photodiode.

Example 10 provides a single package accelerometer and photodiode of example 9, wherein the bottom of the accelerometer is mechanically coupled to the ASIC.

Example 11 provides a single package accelerometer and photodiode of example 10, wherein the of the cap is mechanically coupled to the top of the accelerometer.

Example 12 provides a single package accelerometer and photodiode of example 11 further comprising a package which includes the accelerometer, photodiode, cap and ASIC.

Example 13 provides a single package accelerometer and photodiode of example 12, wherein the package comprises a clear mold compound configured protect any exposed surfaces of the accelerometer, photodiode, cap and ASIC and bond pads.

Example 14 provides a single package accelerometer and photodiode of example 12, wherein the package comprises a glass compound configured protect any exposed surfaces of the accelerometer, photodiode, cap and ASIC and bond pads.

Example 15 provides a single package accelerometer and photodiode of example 1, wherein the single package accelerometer and photodiode is configured to be used in industrial measurement system to measure machine vibrations as well as the motion of the moving parts optically.

Example 16 provides a system in package comprising a substrate, a light source producing a first light disposed on the light source, an accelerometer having a top portion and a bottom portion, a cap having a top portion and bottom portion configured to cover at least part of the top portion of the accelerometer, a photodiode having a top portion and bottom portion disposed in and comprised by the cap, a septum disposed on the substrate between the first light source and the photodiode and, an ASIC in electrical communication with photodiode and accelerometer.

Example 17 provides a system in package of example 16, wherein the ASIC is configured to control synchronous blinking of the first light source for PPG based and other synchronous optical measurements.

Example 18 provides a system in package of example 16, wherein the ASIC is configured to provide an ability to read the available ambient light via the photodiode.

Example 19 provides a system in package of example 16, wherein the system in package is configured to be used in a wearable device.

Example 20 provides a method for making a single package accelerometer and photodiode comprising providing a substrate, mechanically coupling an ASIC to the substrate, bonding an accelerometer to the ASIC, depositing a cap to the accelerometer, the cap configured to cover at least part of the top portion of the accelerometer and, disposing a photodiode into the cap.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

The above-described embodiments may be implemented in any of numerous ways. One or more aspects and embodiments of the present application involving the performance of processes or methods may utilize program instructions executable by a device (e.g., a computer, a processor, or other device) to perform, or control performance of, the processes or methods.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer readable medium or media may be transportable, such that the program or programs stored thereon may be loaded onto one or more different computers or other processors to implement various ones of the aspects described above. In some embodiments, computer readable media may be non-transitory media.

Note that the activities discussed above with reference to the FIGURES which are applicable to any integrated circuit that involves signal processing (for example, gesture signal processing, video signal processing, audio signal processing, analog-to-digital conversion, digital-to-analog conversion), particularly those that can execute specialized software programs or algorithms, some of which may be associated with processing digitized real-time data.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe.

Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smart phone, a mobile phone, an iPad, or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

The terms "program" or "software" are used herein in a generic sense to refer to any type of computer code or set of computer-executable instructions that may be employed to program a computer or other processor to implement various aspects as described above. Additionally, it should be appreciated that according to one aspect, one or more computer programs that when executed perform methods of the present application need not reside on a single computer or processor, but may be distributed in a modular fashion among a number of different computers or processors to implement various aspects of the present application.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In some embodiments, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc.

Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure.

In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Interpretation of Terms

All definitions, as defined and used herein, should be understood to control over dictionary definitions, definitions in documents incorporated by reference, and/or ordinary meanings of the defined terms. Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined.

Elements other than those specifically identified by the "and/or" clause may optionally be present, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "between" is to be inclusive unless indicated otherwise. For example, "between A and B" includes A and B unless indicated otherwise.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

The present invention should therefore not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A single package accelerometer and photodiode comprising:

an accelerometer having a top portion and a bottom portion, the top portion of the accelerometer comprising a MEMS device;

a cap having a top portion and bottom portion, the cap defining an etched cavity configured to enclose the MEMS device of the accelerometer, the cap arranged in a stacked configuration upon a first semiconductor structure comprising the accelerometer; and, wherein the cap comprises a second semiconductor structure comprising a photodiode, the photodiode having a top portion and bottom portion, a photosensitive region of the photodiode located in the top portion of the cap on a surface of the cap opposite the etched cavity, the etched cavity facing the MEMS device; and wherein the accelerometer and photodiode are included as a portion of a commonly shared integrated circuit package.

2. The single package accelerometer and photodiode of claim 1, wherein the cap further comprises a first electrical connection coupled with circuitry configured for biasing protection of the accelerometer.

3. The single package accelerometer and photodiode of claim 1, wherein the bottom portion of the photodiode further comprises an electrical connection coupled with circuitry configured for biasing protection of the accelerometer.

4. The single package accelerometer and photodiode of claim 3, further comprising a second electrical connection in electrical communication with the photodiode.

5. The single package accelerometer and photodiode of claim 4, wherein the second electrical connection is configured to pass through the cap.

6. The single package accelerometer and photodiode of claim 1, wherein the bottom portion of the cap further comprises a metalized layer configured to prevent light from passing into the accelerometer.

7. The single package accelerometer and photodiode of claim 1, further comprising a bond pad disposed in the accelerometer.

8. The single package accelerometer and photodiode of claim 7, further comprising an ASIC.

9. The single package accelerometer and photodiode of claim 8, wherein the ASIC is in electrical communication with the accelerometer and photodiode.

10. The single package accelerometer and photodiode of claim 9, wherein the integrated circuit package comprises an optically transparent material configured to protect any exposed surfaces of the accelerometer, photodiode, cap and ASIC.

11. A system in an integrated circuit package comprising:

a substrate;

a light source disposed on the substrate;

an accelerometer having a top portion and a bottom portion, the top portion of the accelerometer comprising a MEMS device;

a cap having a top portion and bottom portion, the cap defining an etched cavity configured to enclose the MEMS device of the accelerometer, the cap arranged in a stacked configuration upon a first semiconductor structure comprising the accelerometer, the cap comprising a second semiconductor comprising a photodiode, the photodiode having a top portion and bottom portion, a photosensitive region of the photodiode located in the top portion of the cap on a surface of the cap opposite the etched cavity, the etched cavity facing the MEMS device;

a septum disposed on the substrate between the light source and the photodiode, the septum configured to block direct illumination of the photodiode by the light source; and an ASIC in electrical communication with photodiode and accelerometer.

12. The system in the integrated circuit package of claim 11, wherein the ASIC is configured to control synchronous blinking of the light source for PPG based and other synchronous optical measurements.

13. The single package accelerometer and photodiode of claim 1, wherein the cap defining the etched cavity comprises a doped material grown on an intrinsic epitaxial layer, the doped material etched to define the cavity.

14. The system of claim 11, wherein the cap defining the etched cavity comprises a doped material grown on an intrinsic epitaxial layer, the doped material etched to define the cavity.

* * * * *